(12) United States Patent
Chen et al.

(10) Patent No.: US 10,479,985 B1
(45) Date of Patent: Nov. 19, 2019

(54) CELLULASE HAVING IMPROVED ENZYMATIC ACTIVITY

(71) Applicant: Hubei University, Wuhan (CN)

(72) Inventors: Chun-Chi Chen, Wuhan (CN); Jian-Wen Huang, Wuhan (CN); Longhai Dai, Wuhan (CN); Xuejing Yu, Wuhan (CN); Chin-Yu Chen, Wuhan (CN); Shan Wu, Wuhan (CN); Zhichun Zhan, Wuhan (CN); Lilan Zhang, Wuhan (CN); Chao Zhai, Wuhan (CN); Lixin Ma, Wuhan (CN); Rey-Ting Guo, Wuhan (CN)

(73) Assignee: HUBEI UNIVERSITY, Wuhan (CN)

( * ) Notice: Subject to any disclaimer, the term of this patent is extended or adjusted under 35 U.S.C. 154(b) by 0 days.

(21) Appl. No.: 16/406,255

(22) Filed: May 8, 2019

(30) Foreign Application Priority Data

Apr. 16, 2019 (CN) .......................... 2019 1 0303853

(51) Int. Cl.
*C12N 9/24* (2006.01)
*C12N 9/42* (2006.01)

(52) U.S. Cl.
CPC .... *C12N 9/2437* (2013.01); *C12Y 302/01004* (2013.01)

(58) Field of Classification Search
None
See application file for complete search history.

(56) References Cited

PUBLICATIONS

Chen et al., "Crystal structure and genetic modifications of FI-CMCase from Aspergillus aculeatus F-50", Biochem. Biophys. Res. Comm., 2016, vol. 478, pp. 565-572. dx.doi.org/10.1016/j.bbrc.2016.07.101.*
Ooi et al., "Complete nucleotide sequence of a gene coding for Aspergillus aculeatus cellulase (FI-CMCase)", Nuc. Acids Res., 1990, vol. 18, No. 19, p. 5884.*

* cited by examiner

*Primary Examiner* — Suzanne M Noakes
(74) *Attorney, Agent, or Firm* — Kirton McConkie; Evan R. Witt

(57) ABSTRACT

A cellulase having improved enzymatic activity is disclosed. The cellulase has a modified amino acid sequence of SEQ ID NO: 2 or a modified amino acid sequence with at least 80% sequence identity of SEQ ID NO: 2, wherein the modification is a substitution of methionine at position 120 or a corresponding position with asparagine.

6 Claims, 5 Drawing Sheets

Specification includes a Sequence Listing.

caacaagctcaattgtgtgatcaatacgctacttacaccggtggtgtctacactattaacaacaacttgtggggtaaggatgctggttct
Q Q A Q L C D Q Y A T Y T G G V Y T I N N N L W G K D A G S ggttctcaatgtactactgttaactctgcttcttctgctggtacttcttggtctactaagtggaactggtctggaggtgaaaactctgtt
G S Q C T T V N S A S S A G T S W S T K W N W S G G E N S V aagtcttacgctaactctggtttgacttttaacaagaagttggtttcccaaatctctcaaattccaactactgctagatggtcttacgat
K S Y A N S G L F F N K K L V S Q I S Q I P T T A R W S Y D aacactggtattagagctgatgttgcttacgatttgtttactgctgctgatattaaccatgttacttggtctggtgattacgaattgatg
N T G I R A D V A Y D L F T A A D I N H V T W S G D Y E L M atttggttggctagatacggtggtgttcaaccaatcggatctcaaattgctactgctactgttgatggtcaaacttgggaattgtggtac
I W L A R Y G G V Q P I G S Q I A T A T V D G Q T W E L W Y ggtgctaacggttctcaaaagacttactctttttgttgctccaactccaattacttcttttcaaggtgatgttaacgattttttttaagtac
G A N G S Q K T Y S F V A P T P I T S F Q G D V N D F F K Y ttgactcaaaaccacggttttccagcttcttctcaatacttgattactttgcaatttggtactgaaccattcactggtggtccagctact
L T Q N H G F P A S S Q Y L I T L Q F G T E P F T G G P A T tgtctgtttctaactggtccgcttctgttcaatag   - SEQ ID NO: 1
L S V S N W S A S V Q *                - SEQ ID NO: 2

FIG. 1

| Mutant | Primer Sequence |
|--------|-----------------|
| M120N  | 5'- GTCTGGTGATTACGAATTG<u>AAC</u>ATTTGGTTGGCTAGATAC -3'<br>(SEQ ID NO: 3) |

FIG. 3 caacaagctcaattgtgtgatcaatacgctacttacaccggtggtgtctacactattaacaacaacttgtggggtaaggatgctggttct
Q Q A Q L C P Q Y A T Y T G G V Y T I N N N L W G K D A G S ggttctcaatgtactactgttaactctgttcttctgctggtacttcttggtctactaagtggaactggtctggaggtgaaaactctgtt
G S Q C T T V N S A S S A G T S W S T K W N W S G G E N S V aagtcttacgctaactctggttttgacttttaacaagaagttggtttcccaaatctctcaaattccaactactgctagatggtcttacgat
K S Y A N S G L T F D K K L V S Q I S Q I P T T A R W S Y D aacactggtattagagctgatgttgcttacgatttgtttactgctgctgatattaaccatgttacttggtctggtgattacgaattgaac
N T G I R A D V A Y D L F T A A D I N H V T W S G D Y E L N atttggttggctagatacggtggtgttcaaccaatcggatctcaaattgctactgctactgttgatggtcaaacttgggaattgtggtac
I W L A R Y G G V Q P I G S Q I A T A T V D G Q T W E L W Y ggtgctaacggttctcaaaagacttactcttttgttgctccaactccaattacttcttttcaaggtgatgttaacgatttttttaagtac
G A N G S Q K T Y S F V A P T P I T S F Q G D V N D F F K Y ttgactcaaaaccacggttttccagcttcttctcaatacttgattactttgcaatttggtactgaaccattcactggtggtccagctact
L T Q N H G F P A S S Q Y L I T L Q F G T E P F T G G P A T ttgtctgtttctaactggtccgcttctgttcaatag   - SEQ ID NO: 4
L S V S N W S A S V Q *   - SEQ ID NO: 5

FIG. 4

SEQUENCE LISTING

<160> NUMBER OF SEQ ID NOS: 5

<210> SEQ ID NO 1
<211> LENGTH: 666
<212> TYPE: DNA
<213> ORGANISM: Aspergillus aculeatus F-50

<400> SEQUENCE: 1

```
caacaagctc aattgtgtga tcaatacgct acttacaccg gtggtgtcta cactattaac      60
aacaacttgt ggggtaagga tgctggttct ggttctcaat gtactactgt taactctgct     120
tcttctgctg gtacttcttg gtctactaag tggaactggt ctggaggtga aaactctgtt     180
aagtcttacg ctaactctgg tttgactttt aacaagaagt tggtttccca aatctctcaa     240
attccaacta ctgctagatg gtcttacgat aacactggta ttagagctga tgttgcttac     300
gatttgttta ctgctgctga tattaaccat gttacttggt ctggtgatta cgaattgatg     360
atttggttgg ctagatacgg tggtgttcaa ccaatcggat ctcaaattgc tactgctact     420
gttgatggtc aaacttggga attgtggtac ggtgctaacg ttctcaaaa gacttactct     480 tttgttgctc caactccaat tacttctttt caaggtgatg ttaacgattt ttttaagtac     540
ttgactcaaa accacggttt tccagcttct tctcaatact tgattacttt gcaatttggt     600
actgaaccat tcactggtgg tccagctact ttgtctgttt ctaactggtc cgcttctgtt     660
caatag                                                                 666
```

<210> SEQ ID NO 2
<211> LENGTH: 221
<212> TYPE: PRT
<213> ORGANISM: Aspergillus aculeatus F-50

<400> SEQUENCE: 2

```
Gln Gln Ala Gln Leu Cys Asp Gln Tyr Ala Thr Tyr Thr Gly Gly Val
1               5                   10                  15

Tyr Thr Ile Asn Asn Asn Leu Trp Gly Lys Asp Ala Gly Ser Gly Ser
                20                  25                  30

Gln Cys Thr Thr Val Asn Ser Ala Ser Ser Ala Gly Thr Ser Trp Ser
            35                  40                  45

Thr Lys Trp Asn Trp Ser Gly Gly Glu Asn Ser Val Lys Ser Tyr Ala
 50                  55                  60

Asn Ser Gly Leu Thr Phe Asn Lys Lys Leu Val Ser Gln Ile Ser Gln
65                  70                  75                  80

Ile Pro Thr Thr Ala Arg Trp Ser Tyr Asp Asn Thr Gly Ile Arg Ala
                85                  90                  95

Asp Val Ala Tyr Asp Leu Phe Thr Ala Ala Asp Ile Asn His Val Thr
            100                 105                 110

Trp Ser Gly Asp Tyr Glu Leu Met Ile Trp Leu Ala Arg Tyr Gly Gly
        115                 120                 125

Val Gln Pro Ile Gly Ser Gln Ile Ala Thr Ala Thr Val Asp Gly Gln
130                 135                 140

Thr Trp Glu Leu Trp Tyr Gly Ala Asn Gly Ser Gln Lys Thr Tyr Ser
145                 150                 155                 160

Phe Val Ala Pro Thr Pro Ile Ser Phe Gln Gly Asp Val Asn Asp
                165                 170                 175

Phe Phe Lys Tyr Leu Thr Gln Asn His Gly Phe Pro Ala Ser Ser Gln
            180                 185                 190

Tyr Leu Ile Thr Leu Gln Phe Gly Thr Glu Pro Phe Thr Gly Gly Pro
```

```
            195                 200                 205
Ala Thr Leu Ser Val Ser Asn Trp Ser Ala Ser Val Gln
    210                 215                 220
```

<210> SEQ ID NO 3
<211> LENGTH: 40
<212> TYPE: DNA
<213> ORGANISM: Artificial Sequence
<220> FEATURE:
<223> OTHER INFORMATION: Synthetically generated primer

<400> SEQUENCE: 3
gtctggtgat tacgaattga acatttggtt ggctagatac                40

<210> SEQ ID NO 4
<211> LENGTH: 666
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 4
caacaagctc aattgtgtga tcaatacgct acttacaccg gtggtgtcta cactattaac      60
aacaacttgt ggggtaagga tgctggttct ggttctcaat gtactactgt taactctgct    120
tcttctgctg gtacttcttg gtctactaag tggaactggt ctggaggtga aaactctgtt    180
aagtcttacg ctaactctgg tttgactttt aacaagaagt tggtttccca atctctcaa    240 attccaacta ctgctagatg gtcttacgat aacactggta ttagagctga tgttgcttac    300
gatttgttta ctgctgctga tattaaccat gttacttggt ctggtgatta cgaattgaac    360
atttggttgg ctagatacgg tgtgttcaa ccaatcggat ctcaaattgc tactgctact    420
gttgatggtc aaacttggga attgtggtac ggtgctaacg ttctcaaaa gacttactct    480 tttgttgctc aactccaat tacttctttt caaggtgatg ttaacgattt ttttaagtac    540
ttgactcaaa accacggttt tccagcttct tctcaatact tgattacttt gcaatttggt    600
actgaaccat tcactggtgg tccagctact ttgtctgttt ctaactggtc cgcttctgtt    660
caatag                                                                666

<210> SEQ ID NO 5
<211> LENGTH: 221
<212> TYPE: PRT
<213> ORGANISM: Artificial Sequence
<220> FEATURE:
<223> OTHER INFORMATION: Sequence synthetically translated from SEQ ID
      NO: 4

<400> SEQUENCE: 5

```
Gln Gln Ala Gln Leu Cys Asp Gln Tyr Ala Thr Tyr Thr Gly Gly Val
1               5                   10                  15

Tyr Thr Ile Asn Asn Asn Leu Trp Gly Lys Asp Ala Gly Ser Gly Ser
            20                  25                  30

Gln Cys Thr Thr Val Asn Ser Ala Ser Ser Ala Gly Thr Ser Trp Ser
        35                  40                  45

Thr Lys Trp Asn Trp Ser Gly Gly Glu Asn Ser Val Lys Ser Tyr Ala
    50                  55                  60

Asn Ser Gly Leu Thr Phe Asn Lys Lys Leu Val Ser Gln Ile Ser Gln
65                  70                  75                  80

Ile Pro Thr Thr Ala Arg Trp Ser Tyr Asp Asn Thr Gly Ile Arg Ala
```

-continued

```
                        85                      90                      95
Asp Val Ala Tyr Asp Leu Phe Thr Ala Ala Asp Ile Asn His Val Thr
                100                     105                 110

Trp Ser Gly Asp Tyr Glu Leu Asn Ile Trp Leu Ala Arg Tyr Gly Gly
            115                     120                 125

Val Gln Pro Ile Gly Ser Gln Ile Ala Thr Ala Thr Val Asp Gly Gln
        130                     135                 140

Thr Trp Glu Leu Trp Tyr Gly Ala Asn Gly Ser Gln Lys Thr Tyr Ser
145                     150                     155                 160

Phe Val Ala Pro Thr Pro Ile Thr Ser Phe Gln Gly Asp Val Asn Asp
                    165                     170                 175

Phe Phe Lys Tyr Leu Thr Gln Asn His Gly Phe Pro Ala Ser Ser Gln
                180                     185                 190

Tyr Leu Ile Thr Leu Gln Phe Gly Thr Glu Pro Phe Thr Gly Gly Pro
            195                     200                 205

Ala Thr Leu Ser Val Ser Asn Trp Ser Ala Ser Val Gln
    210                     215                 220
```

CELLULASE HAVING IMPROVED ENZYMATIC ACTIVITY

FIELD OF THE INVENTION

The present invention relates to a cellulase, and more particularly to a cellulase having improved enzymatic activity.

BACKGROUND OF THE INVENTION

Cellulose is the major component of plant cell wall which constitutes 35-50% of the dry mass of plants, and thus is the most abundant renewable biomass on earth. Cellulose is a polysaccharide that is composed of glucose units linked by 1,4-β-glycosidic bonds. The highly compacted structure of cellulose microfibril contributes to biomass recalcitrance and resistance to microbial attack. Cellulose can be degraded into glucose and utilized as an energy source by numerous microorganisms, including bacteria, yeast and fungi. The complete degradation of cellulose requires several enzymes such as: endo-1,4-β-D-glucanase (endoglucanase, EC 3.2.1.4), cellobiohydrolase (EC 3.2.1.91), and β-glucosidase (EC 3.2.1.21). Among these cellulases, endoglucanase, which randomly hydrolyzes β-glycosidic bonds to cleave cellulose into smaller fragments, is the key cellulolytic enzyme. Endoglucanases are present in various microorganisms including fungi and bacteria. Based on their amino acid sequence similarities, cellulases are classified into different glycoside hydrolase (GH) families including GH 5, 6, 10, 12, 18, 45, and 74.

In recent years, the use of enzymatic hydrolysis of cellulose has been studied extensively and endoglucanases were widely applied in various industries, such as animal feed, food manufacture, textile industry and biofuel production. According to different industrial needs, cellulase is required to be suitable for different appropriate working conditions. Therefore, many scientists try to find better cellulases for industrial use by either searching new genes in nature or modifying existing enzymes. In many strategies for modifying the enzyme, protein engineering by rational design based on structural analysis is one of the major strategies for improvement of industrial enzyme. In this strategy, to increase the enzymatic activity is a key point of the industrial enzyme improvement. The higher enzyme activity represents the cost reduction of the industrial process, which further enhances the commercial profit.

Therefore, the present invention intends to analyze the enzyme structure of the cellulase for finding out the key amino acid important to the enzymatic activity and further modify the enzyme, so as to improve the enzymatic activity of the cellulase and thus increase the industrial application value of the cellulase.

SUMMARY OF THE INVENTION

An object of the present invention is to modify a cellulase by means of structural analysis and site-directed mutagenesis for efficiently improving the enzymatic activity and further increasing the industrial value of the cellulase.

According to an aspect of the present invention, there is provided a cellulase having a modified amino acid sequence of SEQ ID NO: 2 or a modified amino acid sequence with at least 80% sequence identity of SEQ ID NO: 2, wherein the modification is a substitution of methionine at position 120 or a corresponding position with asparagine.

In an embodiment, a gene encoding the amino acid sequence of SEQ ID NO: 2 is FI-CMCase gene isolated from *Aspergillus aculeatus* F-50.

In an embodiment, the cellulase is an endoglucanase.

In an embodiment, the cellulase has the full length amino acid sequence of SEQ ID NO: 5.

According to another aspect of the present invention, there is provided a nucleic acid encoding the aforesaid cellulase, and a recombinant plasmid comprising the aforesaid nucleic acid.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the nucleotide sequence and the amino acid sequence of the wild type FI-CMCase;

FIG. 3 shows the primer sequence for site-directed mutagenesis;

FIG. 4 shows the nucleotide sequence and the amino acid sequence of the M120N mutant of FI-CMCase.

DETAILED DESCRIPTION OF THE PREFERRED EMBODIMENT

Figure 2:
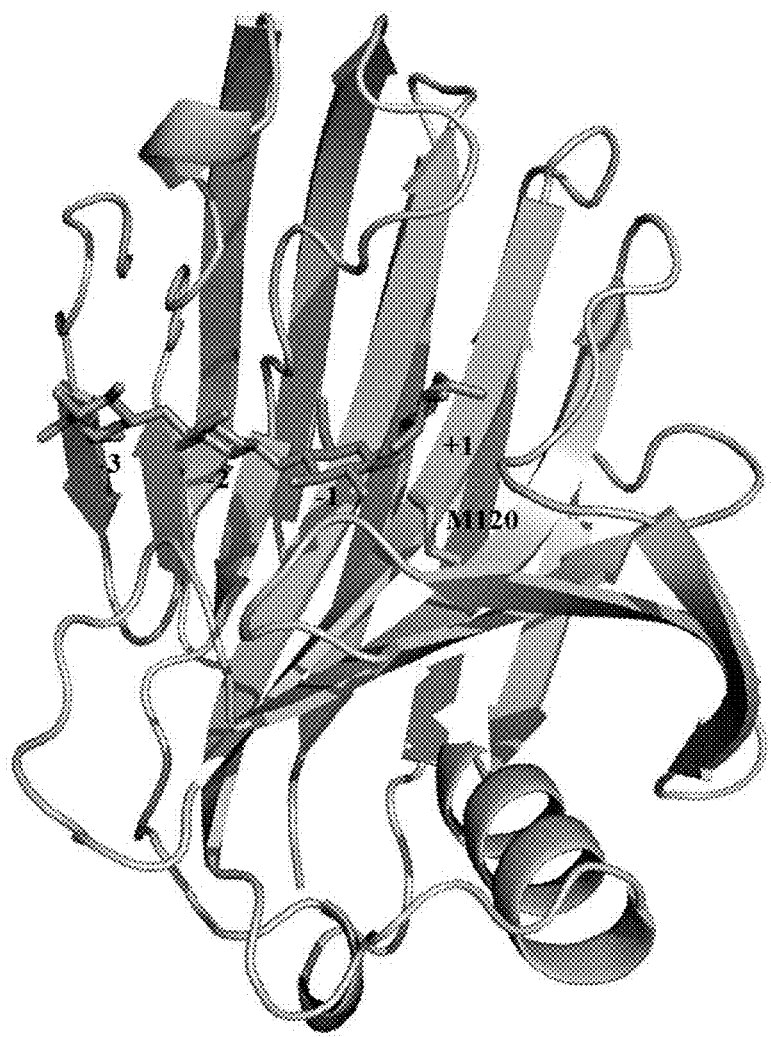
FIG. 2 shows the protein structure of the wild type FI-CMCase in complex with cellotetraose.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

A cellulase gene of FI-carboxymethylcellulase (FI-CMCase) was isolated from the fungus *Aspergillus aculeatus* F-50, which is known to produce many cellulolytic enzymes. The FI-CMCase gene was subsequently expressed and characterized in *Escherichia coli* and *Saccharomyces cerevisiae*. The expressed protein FI-CMCase is an endoglucanase with optimal pH and temperature of 5.0 and 50° C., respectively. In the present invention, it is found that FI-CMCase can be efficiently expressed and produced using *Pichia pastoris*, which is commonly used in the industry. In addition, the recombinant protein FI-CMCase expressed in *P. pastoris* displays high enzymatic activity towards carboxymethyl cellulose (CMC) and filter paper. These results substantiate the idea that FI-CMCase is a potential candidate for commercial utilization. In order to improve the industrial application value of this enzyme, the protein structure of FI-CMCase in complex with its substrate was solved by X-ray crystallography.

The FI-CMCase gene (GenBank accession No. X52525.1) was obtained from *A. aculeatus* F-50, and FIG. 1 shows the nucleotide sequence and the amino acid sequence of the wild type FI-CMCase, wherein the FI-CMCase gene consists of 666 base pairs (SEQ ID NO: 1, including the stop codon) and encodes 221 amino acids (SEQ ID NO: 2). First, the FI-CMCase gene was constructed into pPICZαA vector by using EcoRI and NotI sites. The plasmid DNA was linearized by PmeI and transformed into the *P. pastoris* X33 strain by electroporation. The transformants were selected on YPD (1% yeast extract, 2% peptone, 2% glucose, 2% agar) plates containing 100 µg/ml Zeocin and incubated at 30° C. for 2 days. The protein expression of the transformants was tested by the following small-scale expression. The selected colonies were inoculated in 5 ml YPD medium and then amplified in 50 ml BMGY at 30° C. for 24 hours. The cells were harvested by centrifugation and resuspended in 20 ml BMMY to induce protein expression. Afterward, the transformants with higher expression level were chosen for scale-up expression. The cells were inoculated in 5 ml YPD and then amplified in 500 ml BMGY at 30° C. for 24 hours. The cells were harvested and then resuspended in 500 ml BMMY. A total of 0.5% methanol was supplemented every 24 hours to induce protein expression for 4 consecutive days. For protein purification, the supernatant was collected by centrifugation and then dialyzed twice against 5 L of buffer containing 25 mM Tris, pH 7.5. The proteins were purified by FPLC system using DEAE column. The purified proteins were finally concentrated to 10 mg/ml in 25 mM Tris-HCl pH 7.5, 150 mM NaCl and the purity was checked by SDS-PAGE analysis.

To solve the protein structure of FI-CMCase by X-ray crystallography, the protein was crystallized by using sitting-drop vapor diffusion method. The initial crystals of FI-CMCase were obtained within 10 days using commercial Crystal Screen kit and the better crystals were obtained from the reservoir solution containing 0.3 M zinc acetate dihydrate, 0.1 M sodium cacodylate pH 6.5, and 19% (w/v) polyethylene glycol 8000 at room temperature for 10 days. The phase problem was solved by molecular replacement method. The complex crystals of FI-CMCase were obtained by soaking the crystals with 10 mM cellotetraose.

FIG. 2 shows the protein structure of the wild type FI-CMCase in complex with cellotetraose. The protein structure of FI-CMCase showed the β-jelly roll protein fold which is typical of GH 12 family enzymes. According to the enzyme-substrate complex structure, it was observed that the residue Met120 is located in the active site and has interaction with cellotetraose, and considered this residue may be important to the catalytic reaction of FI-CMCase. Therefore, Met120 was chosen and mutated to asparagine by site-directed mutagenesis to enhance its enzymatic activity.

The enzyme modification processes and the resulted cellulase protein are described in detail as follows. The mutant was prepared by using commercial site-directed mutagenesis kit with FI-CMCase gene as a template. FIG. 3 shows the primer sequence for site-directed mutagenesis to substitute the methionine (M) at position 120 of the FI-CMCase protein with asparagine (N), wherein M120N means the methionine (M) at position 120 was substituted by asparagine (N), and the primer sequence was numbered as SEQ ID NO: 3. The original template was removed via DpnI digestion under 37° C. After that, the mutated gene was transformed into E. coli and then confirmed by DNA sequencing.

FIG. 4 shows the nucleotide sequence and the amino acid sequence of the M120N mutant of FI-CMCase, wherein the M120N mutant gene also consists of 666 base pairs (SEQ ID NO: 4, including the stop codon) and encodes 221 amino acids (SEQ ID NO: 5), and the methionine (M) at position 120 was substituted with asparagine (N).

Finally, the mutated gene was transformed into P. pastoris for protein expression as previously mentioned. The supernatants of the wild type enzyme and the M120N mutant were tested for cellulase activity assay under the same protein concentration. The cellulase activity was determined by dinitrosalicylic acid (DNS) method. In the embodiment, equal amounts of enzyme solution (50 mM sodium citrate buffer, pH 4.8) and 1% (w/v) carboxymethyl cellulose (CMC) were co-incubated in a water bath at 50° C. for 10 min. The reaction was mixed with 1% DNS and then incubated at 100° C. boiled water for 10 min to remove residual enzyme activity. After cooling in cold water bath for 5 min, the 540 nm absorbance of the reaction solution was measured for calculation of the enzymatic activity. One unit of activity is defined as the amount of enzyme that releases 1 µmole product per minute.

Figure 5:
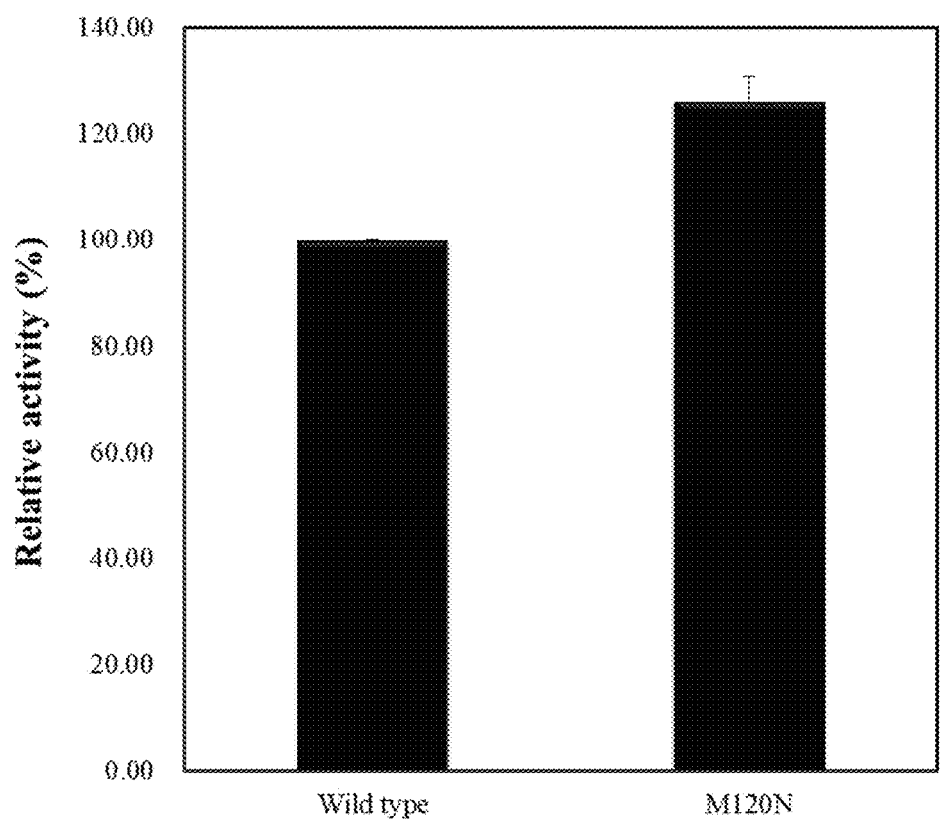
FIG. 5 shows the cellulase activity analysis of the wild type enzyme and the M120N mutant.

FIG. 5 shows the cellulase activity analysis of the wild type enzyme and the M120N mutant, wherein the protein concentrations of these samples were normalized and the cellulase activity of the wild type enzyme was set to 100%. It was observed that the specific activity (unit/mg) of the M120N mutant was higher than the wild type enzyme. Especially, the M120N mutant significantly increased in the specific activity of 26% when compared to the wild type enzyme. Besides, the expression level of the M120N mutant was similar to the wild type enzyme. These results indicated that the total activity of the enzyme was increased when Met120 was mutated to asparagine. That means the M120N mutant has higher economic value of industrial application when compared to the wild type enzyme.

Besides, the enzymes usually have some variations among different species, but still have the same function, and most of them have at least 80% identity in amino acid sequence. Obviously, the enzymes are allowed to have some amino acid sequence variations but still maintain the enzyme function. In other words, the modified cellulase sequence provided in the present invention is not limited to the sequence of SEQ ID NO: 2 having the substitution of methionine at position 120 with asparagine, but also includes the sequence with at least 80% sequence identity of SEQ ID NO: 2 having the substitution of methionine at a corresponding position with asparagine.

Because the industrial processes usually involve various harsh conditions, the industrial enzymes should be modified to satisfy industrial requirements, such as excellent thermostability, a broader range of pH adaptability, and higher enzymatic activity. To reach the goals, the structural information of the enzyme is required to better understand the catalytic mechanism and design the subsequent protein engineering, so as to improve the enzyme properties and efficiency. Therefore, to increase the industrial value of the cellulase FI-CMCase, the present invention solved its enzyme-substrate complex structure and chose the residue Met120 located in the active site of FI-CMCase for further modification. It was observed that the cellulase activity of the M120N mutant was significantly higher than that of the wild type enzyme. That is to say, the present invention successfully improves the enzymatic activity of the cellulase and further increases its economic value of industrial application.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A cellulase having a modified amino acid sequence of SEQ ID NO: 2 or a modified amino acid sequence with at least 80% sequence identity of SEQ ID NO: 2, wherein the modification is a substitution of methionine at position 120 or a corresponding position with asparagine.

2. The cellulase according to claim 1 wherein a gene encoding the amino acid sequence of SEQ ID NO: 2 is FI-CMCase gene isolated from *Aspergillus aculeatus* F-50.

3. The cellulase according to claim 1 being an endoglucanase.

4. The cellulase according to claim 1 having the full length amino acid sequence of SEQ ID NO: 5.

5. A nucleic acid encoding the cellulase of claim 1.

6. A recombinant plasmid comprising the nucleic acid of claim 5.

* * * * *